United States Patent [19]

Morinaga et al.

[11] Patent Number: 5,426,050
[45] Date of Patent: Jun. 20, 1995

[54] PLASMID VECTORS FOR EXPRESSION OF GENES IN CORYNEFORM BACTERIA

[75] Inventors: Yasushi Morinaga; Makoto Tsuchiya, both of Kawasaki, Japan

[73] Assignee: Ajinomoto Co., Inc., Tokyo, Japan

[21] Appl. No.: 167,112

[22] Filed: Dec. 16, 1993

Related U.S. Application Data

[63] Continuation of Ser. No. 35,502, Mar. 22, 1993, abandoned, which is a continuation of Ser. No. 774,374, Oct. 10, 1991, abandoned, which is a continuation of Ser. No. 339,876, Apr. 18, 1989, abandoned, which is a continuation of Ser. No. 901,642, Aug. 29, 1986, abandoned.

[30] Foreign Application Priority Data

Sep. 6, 1985 [JP] Japan .............................. 60-197277
Jun. 13, 1986 [JP] Japan .............................. 61-137833

[51] Int. Cl.$^6$ ..................... C12N 1/21; C12N 15/77
[52] U.S. Cl. ..................... 435/252.32; 435/320.1
[58] Field of Search ............... 435/69.1, 172.3, 320.1, 435/252.32; 536/23.1, 24.1

[56] References Cited

U.S. PATENT DOCUMENTS

| | | | |
|---|---|---|---|
| 4,371,614 | 2/1983 | Anderson et al. | 435/108 |
| 4,601,983 | 7/1986 | Nakamori et al. | 435/115 |
| 4,643,969 | 2/1987 | Inouye et al. | 435/69.1 |
| 4,649,119 | 3/1987 | Sinskey et al. | 435/320.1 |
| 4,711,845 | 12/1987 | Gelfand et al. | 435/69.1 |
| 4,753,876 | 6/1988 | Hemming et al. | 435/34 |
| 4,912,046 | 3/1990 | Henner et al. | 435/252.3 |
| 4,946,781 | 8/1990 | Nakamori et al. | 435/115 |

OTHER PUBLICATIONS

Smith et al. *Applied and Environmental Microbiology* 51:634–9, 1986 (Mar.).
Kelley et al. (1985), PNAS, vol. 82, pp. 483–487.
C. J. Thompson et al, *Gene,* vol. 20, pp. 51–62 (1982).
J. L. Schottel et al, *J. Bacteriology,* vol. 146, pp. 360–368 (1981).
*Agric. Biol. Chem.,* vol. 44, pp. 367–381 (1980).
"Genetics and Biotechnology of Bacilli", edited by Ganesan et al (Academic Press 1984).
Nature, 293, 309–311 (1981) Goldfarb et al.
"Molecular Breeding and Genetics of Applied Microorganisms", edited by Sakaguchi et al (1980), pp. 1–7.

*Primary Examiner*—Richard A. Schwartz
*Assistant Examiner*—Philip W. Carter
*Attorney, Agent, or Firm*—Oblon, Spivak, McClelland, Maier & Neustadt

[57] ABSTRACT

A recombinant plasmid vector is provided which is capable of replicating and expressing in a Coryneform bacterial cell, which plasmid vector is pEC 701, pEC 702, pEC 801, pEC 830 or pEC 901.

2 Claims, 9 Drawing Sheets

PLASMID VECTORS FOR EXPRESSION OF GENES IN CORYNEFORM BACTERIA

This application is a Continuation of application Ser. No. 08/035,502, filed on Mar. 22, 1993, now abandoned which was a Continuation of application Ser. No. 07/774,374, filed on Oct. 10, 1991, now abandoned, which was a Continuation of application Ser. No. 07/339,876, filed on Apr. 18, 1989, now abandoned, which was a Continuation of application Ser. No. 06/901,642, filed on Aug. 29, 1986, now abandoned.

BACKGROUND OF THE INVENTION

1. Field of the Invention

The present invention relates to a method for controlling phenotypic gene expression of Coryneform bacteria.

2. Description of the Prior Art

Coryneform bacteria are microorganisms which are industrially important. Many Coryneform bacteria which produce large quantities of L-glutamic acid are known, including their mutants producing amino acids such as lysine, etc., and purine nucleotides such as inosinic acid, etc.

On the other hand, breeding and improvement of microorganisms for industrial use utilizing recombinant DNA techniques have been recently attempted in, for example, *Escherichia coli*. With respect to Coryneform bacteria, some vectors are known as growing in these microorganisms as a host and expressing chemical resistance as a marker (e.g., Published European Patent Application No. 93611), but no method for artificially regulating inserted foreign genes has been discovered. Therefore, it has been difficult to regulate gene expression artificially while expressing foreign genes using Coryneform bacteria as a host.

SUMMARY OF THE INVENTION

Accordingly, it is an object of the present invention to provide a plasmid vector capable of regulating foreign gene expression in Coryneform bacterial cells.

It is a further object of this invention to provide a method for regulating the expression of foreign genes in Coryneform bacterial cells.

These and other objects of the present invention as will hereinafter become more readily apparent have been accomplished by providing a plasmid vector capable of replicating in a Coryneform bacterial cell having a base sequence (a) functioning as a promotor in the Coryneform bacterium, a base sequence (b) functioning as an operator downstream from the base sequence (a), a base sequence (c) functioning as a site for ribosome binding in a Coryneform bacterial cell, a base sequence (d) functioning as a translation initiation site, and a gene to be expressed, which is directly ligated with base sequence (d) and bears a gene coding for a repressor protein capable of binding to the base sequence (b) functioning as an operator.

The invention further comprises a method for regulating gene expression in Coryneform bacterial cells, which involves using a Coryneform bacterial cell having a plasmid vector comprising base sequences (a)–(d) and the gene to be expressed which is directly ligated with base sequence (d) and bearing a gene coding for a repressor protein.

BRIEF DESCRIPTION OF THE DRAWINGS

A more complete appreciation of the invention, and many of the attendant advantages thereof will be readily obtained as the invention becomes better understood by reference to the following detailed description when considered in connection with the accompanying drawings, wherein.

P : Pst I
C : Cla I
H : Hind III
B : BamH I
$Km^r$: kanamycin-resistant gene
$Cm^s$ : structural gene region of chloramphenicol-resistant gene.

Figure 2:
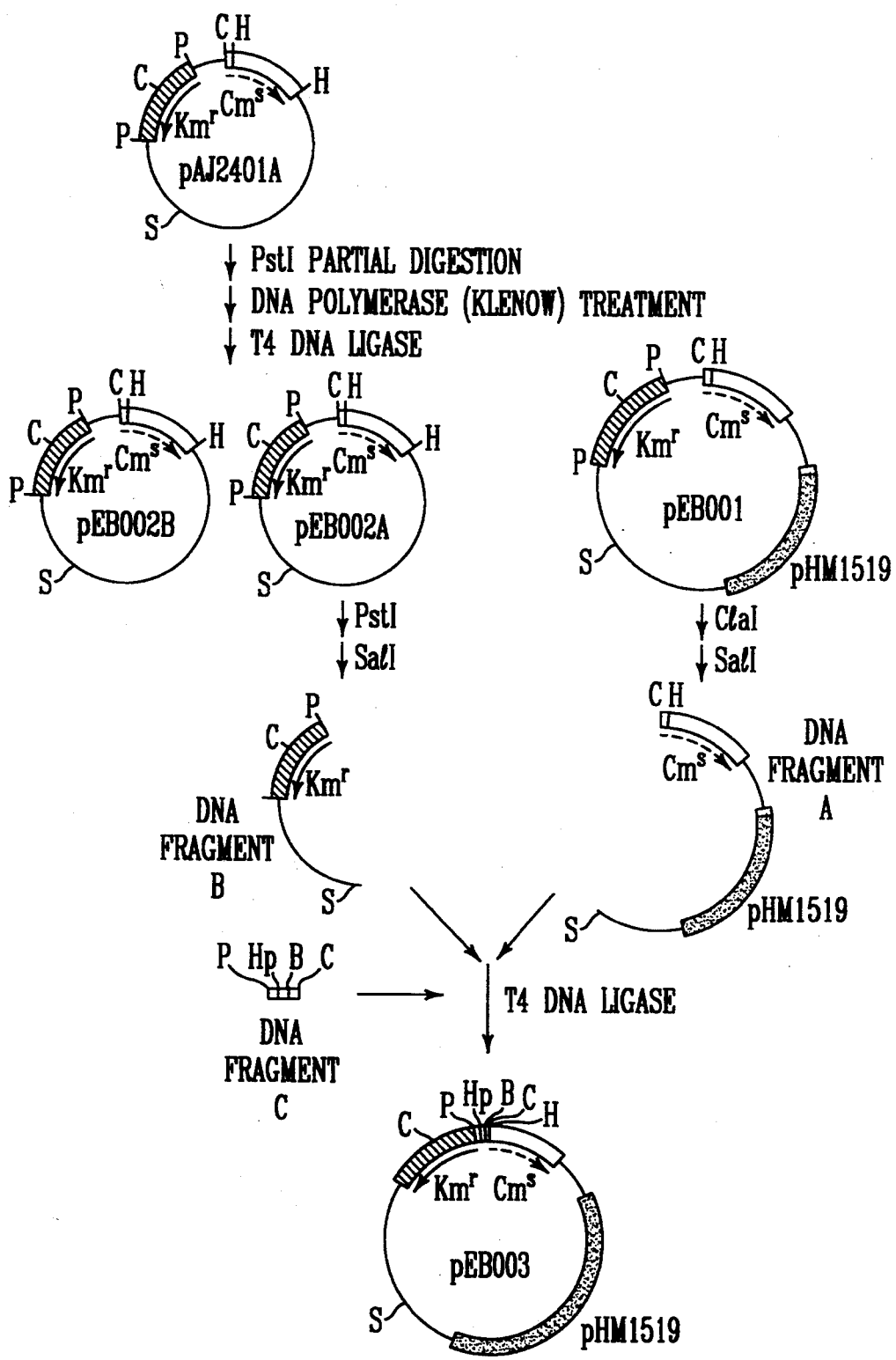
Figure 3:
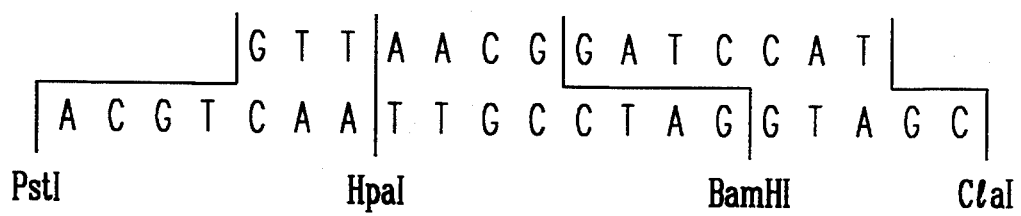

FIG. 2 is a drawing explaining the procedure for constructing a promoter-detecting vector pEB 003. The abbreviations have the following meanings:

P : Pst I
C : Cla I
H : Hind III
B : BamH I
S : Sal I
$Km^r$: kanamycin-resistant gene
$Cm^s$ : structural gene region of chloramphenicol-resistant gene, FIG. 3 shows a structure of DNA fragment C used for the formation of a promoter-detecting vector pEB 003.

Figure 4:
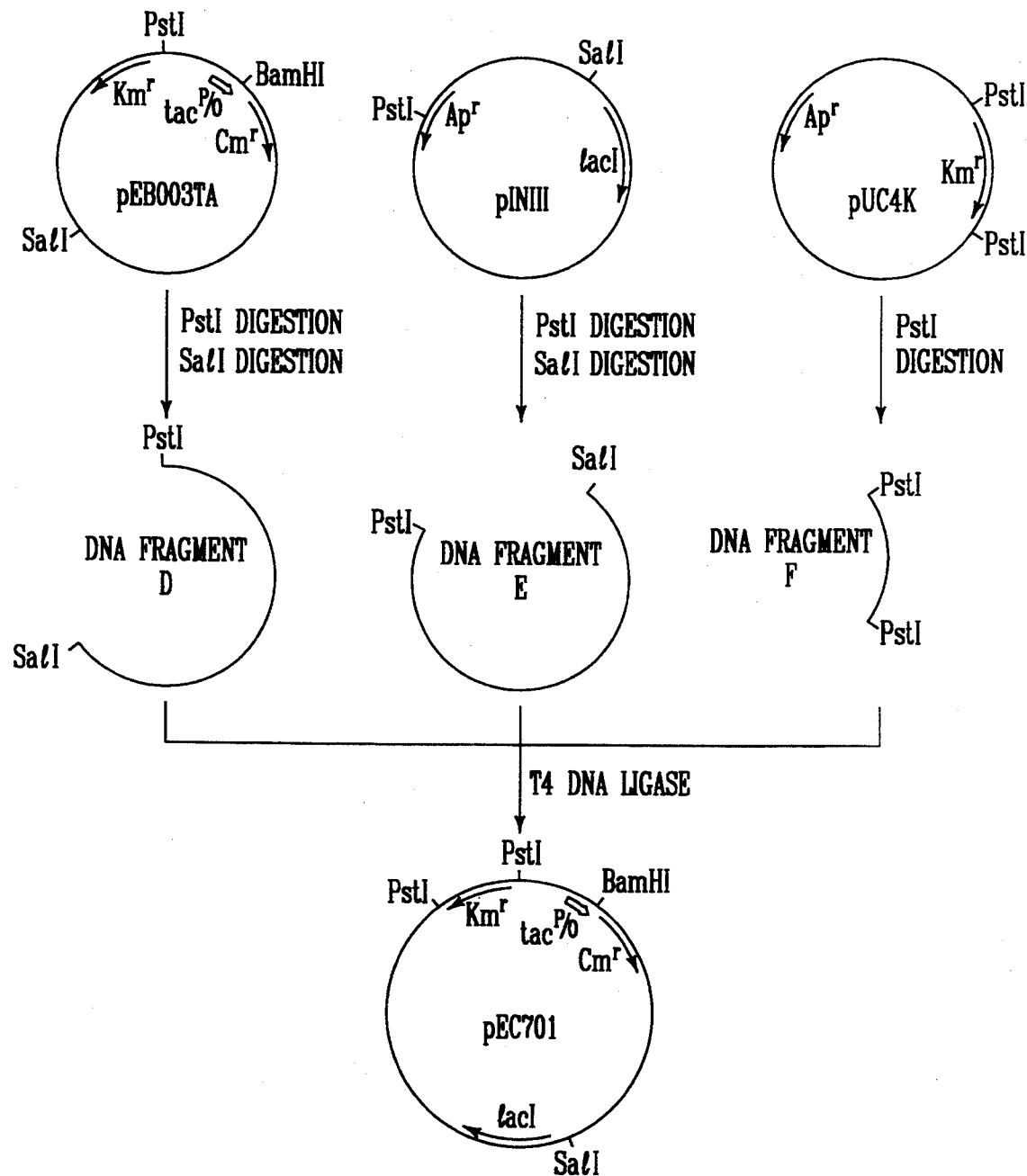

FIG. 4 is a drawing explaining the procedure for constructing a gene expression-regulating vector pEC 701.

Figure 5:
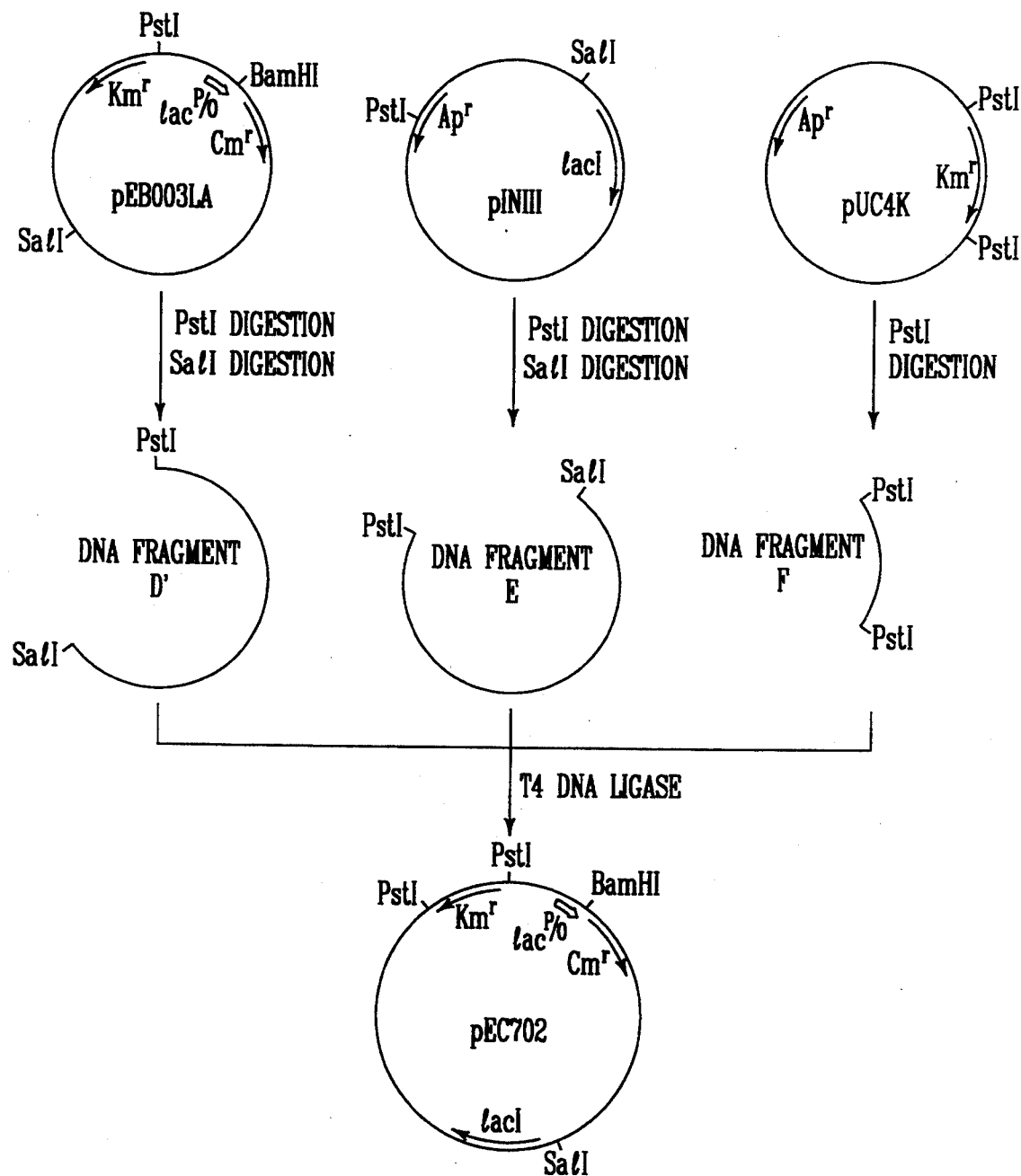

FIG. 5 is a drawing explaining the procedure for constructing a gene expression-regulating vector pEC 702.

Figure 6:
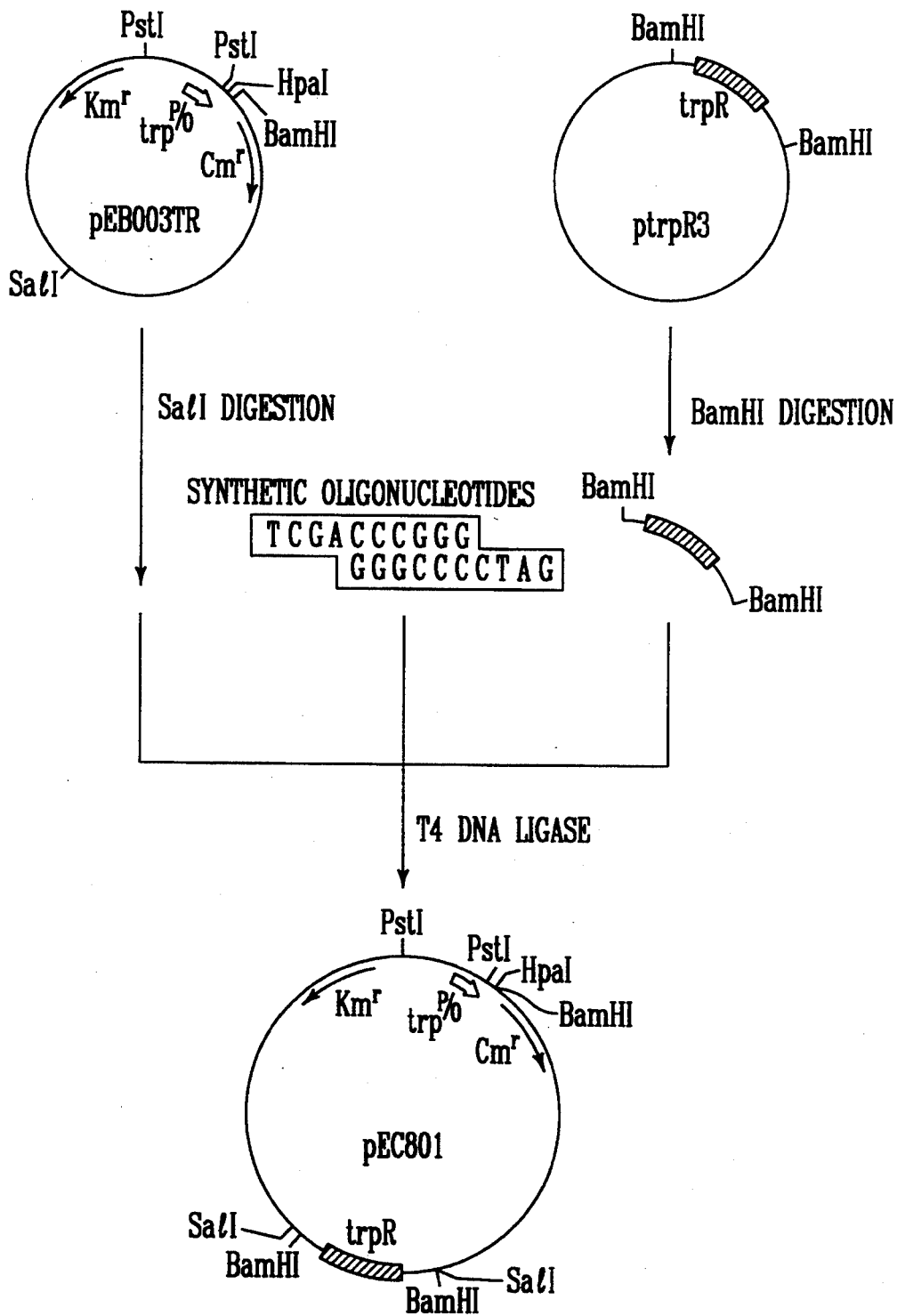

FIG. 6 is a drawing explaining the procedure for constructing a gene expression-regulating vector pEC 801.

Figure 7:
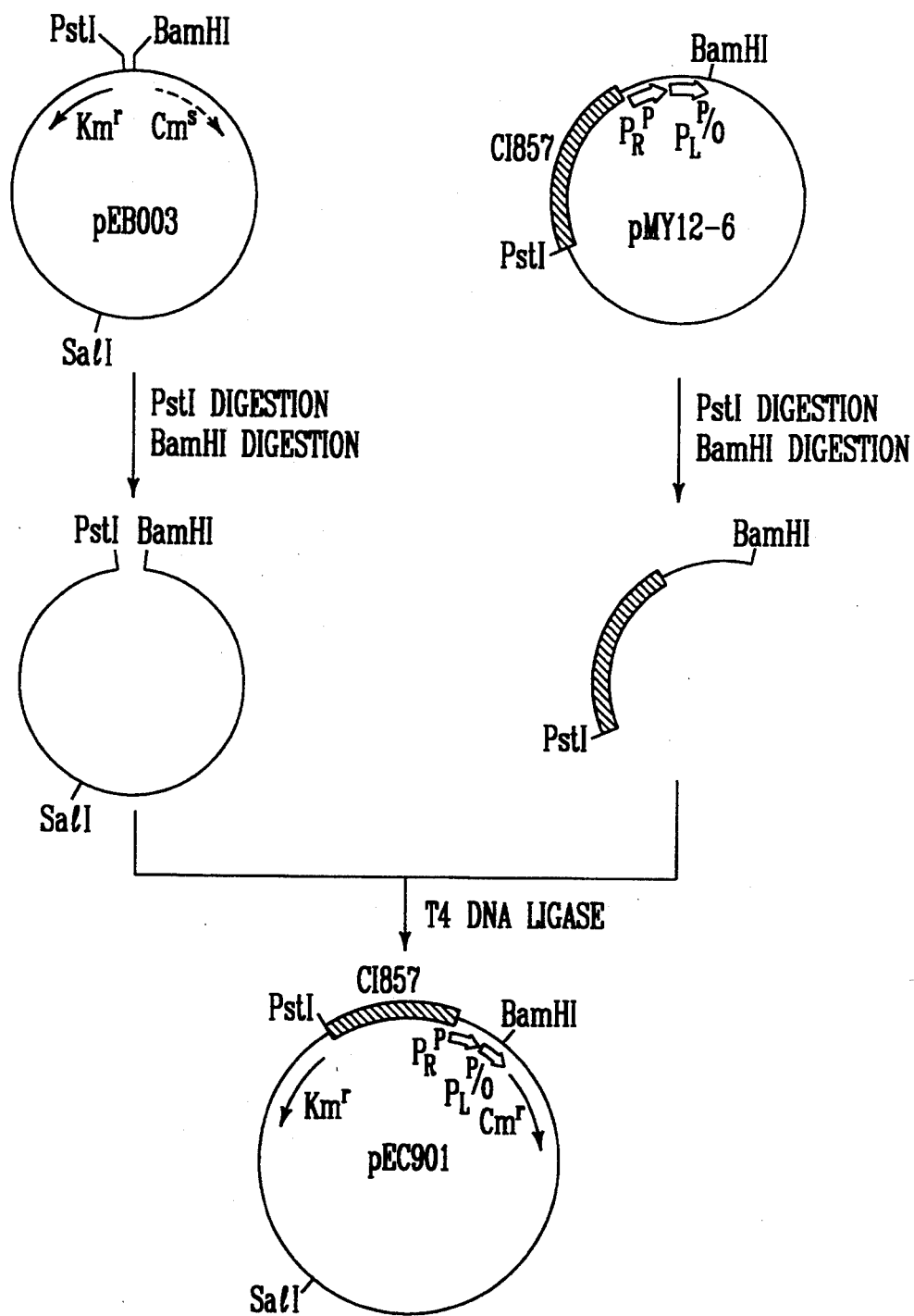

FIG. 7 is a drawing explaining the procedure for constructing a gene expression-regulating vector pEC 901.

Figure 8:
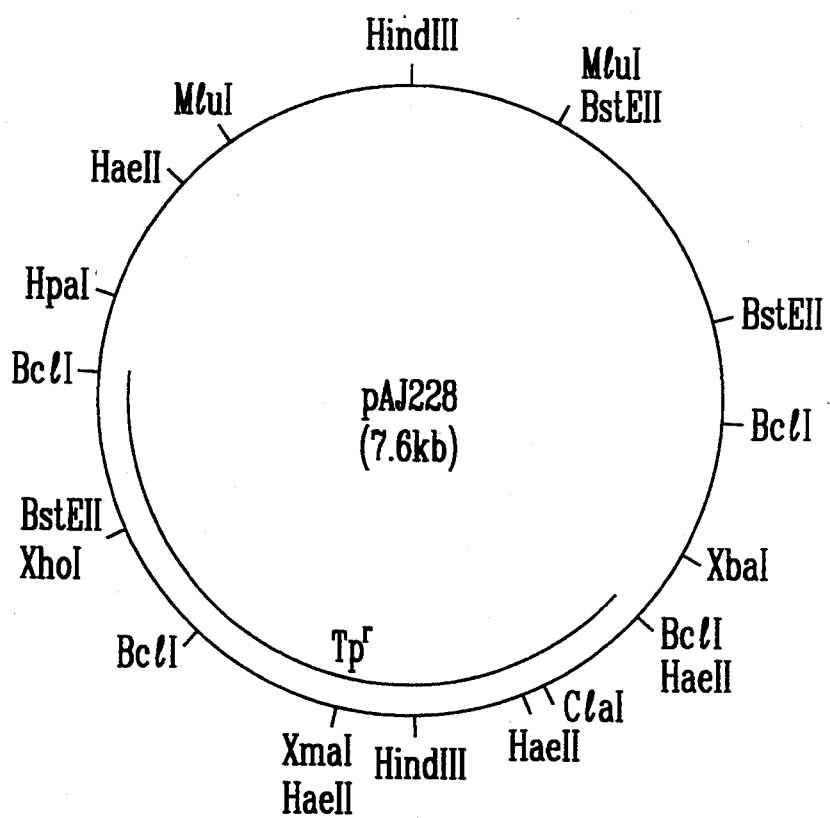

FIG. 8 shows the structure of trimethoprim-resistant vector pAJ 228.

Figure 9:
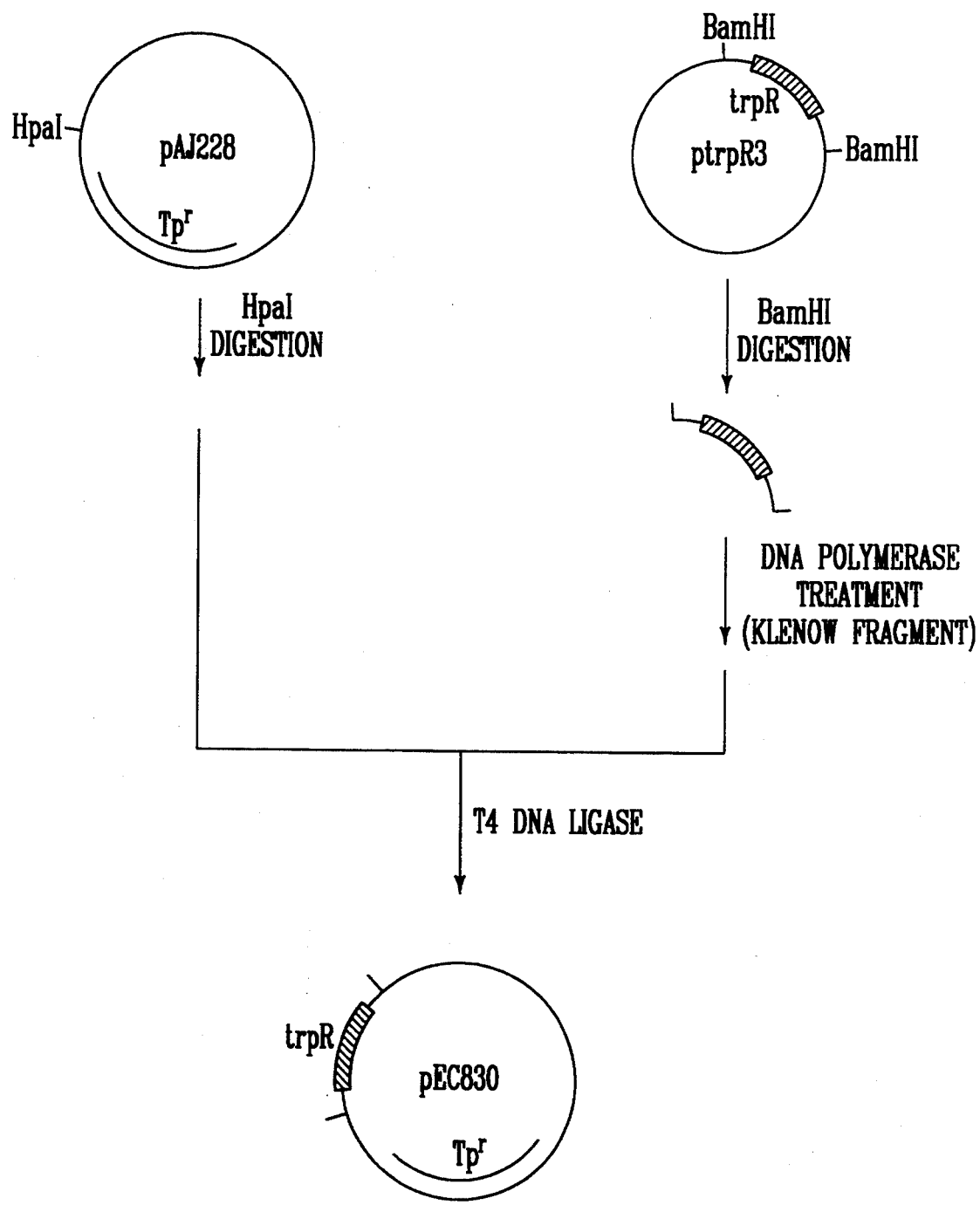

FIG. 9 is a drawing explaining the procedure for constructing a gene expression-regulating vector pEC 830.

DESCRIPTION OF THE PREFERRED EMBODIMENTS

Coryneform bacteria are aerobic, gram-positive rods, non-acid fast and described in Bergey's *Manual of Determinative Bacteriology*, 8th edition, page 599 (1974). Examples of wild strains of Coryneform bacteria which can be utilized as host bacteria in the present invention include the following:

Brevibacterium divaricatum ATCC 14020,
Brevibacterium saccharolyticum ATCC 14066,
Brevibacterium immariophilum ATCC 14068,
Brevibacterium lactofermentum ATCC 13869,
Brevibacterium roseum ATCC 13825,
Brevibacterium flavum ATCC 13826,
Brevibacterium thiogenitalis ATCC 19240,
Corynebacterium acetoacidophilum ATCC 13870,
Corynebacterium acetoglutamicum ATCC 15806,
Corynebacterium callunae ATCC 15991, Corynebacterium glutamicum ATCC 13032, 13060,
Corynebacterium lilium ATCC 15990,
Corynebacterium melassecola ATCC 17965, and
Microbacterium ammoniaphilum ATCC 15354.

Coryneform bacteria include mutants which are derived from these glutamic acid-producing bacteria or have lost glutamic acid productivity, and mutants which produce amino acids such as lysine, arginine, etc., purine nucleosides such as inosine, etc., purine nucleotides such as inosine-5'-mono-phosphate, etc. and other products. Any plasmid that proliferates in Coryneform bacterial cells can be used as the plasmid capable of replicating in Coryneform bacterial cells. Examples of wild strains of such a plasmid include the following:

(1) pAM 330: cf. Published Unexamined Japanese Patent Application 67699/83
(2) pHM 1519: cf. Published Unexamined Japanese Patent Application 77895/83
(3) pCG 1: cf. Published Unexamined Japanese Patent Application 134500/82
(4) pCG 2: cf. Published Unexamined Japanese Patent Application 35197/83
(5) pCG 4: cf. Published Unexamined Japanese Patent Application 183799/82.

As the plasmid capable of replicating in Coryneform bacterial cells, it is sufficient to have contained therein an initiation site for replication of these wild plasmids. Therefore, there is no particular problem even though the vector contains DNA's other than the initiation site for replication.

Any sequence can be used as the base sequence (a) functioning as a promoter as long as it is a base sequence functioning as a promoter in Coryneform bacterial cells. Of course, the base sequence can be a base sequence of a promoter derived from Coryneform bacteria and base sequences of foreign promoters such as base sequences of various promoters derived from *Escherichia coli* (D. K. Hawley and W. McClure, Nucleic Acids Research 11, 2237-2255 (1983)), and others.

The base sequence (b) functioning as an operator can be any base sequence as long as the repressor protein can be bound thereto. Of course, the base sequence (b) includes a base sequence of an operator derived from Coryneform bacteria, base sequences of various operators derived from *Escherichia coli*, e.g., base sequences of foreign operators such as a lac operator, a trp operator (Kenzo Nakamura, KAGAKU-NORYOIKI, 37(5), 349-362 (1983)), a λ operator (Erik Remaut et al, Gene, 15, 81-93 (1981)), an operator of a phosphatase operon (Hideo Shinagawa et al, Journal of Bacteriology, Japan, 40, 211 (1985)), and others. The above-mentioned references are incorporated herein the same as if each were individually reproduced in its entirety at this location.

The base sequence (c) is a base sequence comprising 4 base pairs rich in adenine (A) and guanine (G). In particular, the upstream 2 base pairs are rich in A and the downstream 2 base pairs are rich in G. The distance between the base sequence (d) and the base sequence (c) is 7 base pairs or more but when the number of base pairs is large (exceeds 20 base pairs), the efficiency of desired gene expression declines. A preferred range of base pair distance is 10 to 15 base pairs between base sequence (d) and base sequence (c).

The investigations by the present inventors revealed that in the base sequence (d), ATG or GTG functions as a translation initiation codon in Coryneform bacteria.

The gene to be expressed, which is directly ligated to the base sequence (d), may be any gene derived from microorganisms such as bacteria belonging to the genus Coryneform, bacteria belonging to the genus Streptomyces, yeast belonging to the genus Saccharomyces, bacteria belonging to the genus Escherichia and Bacillus, and so on, genes derived from animals, artificially synthesized genes, and the like. Further, the expression products of the gene to be expressed are enzymes which participate in production of amino acids, glucose, vitamins, etc., improvement in quality of oils and fats, proteins, starch, etc., modification of antibiotics, chemical substances, etc. such as hydrolase, transaminase, decarboxylase, phosphotransferase, etc., as well as immune modulators such as lymphokines, etc., physiologically active proteins such as animal hormones, etc.

As the gene coding for the repressor protein, any gene can be used as long as the protein the gene encodes can bind to the base sequence (b) of the operator used in Coryneform bacteria and the gene has a property such that the binding activity can be artifically controlled. Such a gene includes, of course, a repressor gene derived from Coryneform bacteria, various repressor genes derived from *Escherichia coli*, e.g., the lac repressor (lac I) (Miller and Reznikoffs, The Operon, Cold Spring Harbor Lab., pp. 31-88 (1978)), the trp repressor (trp R) (R. L. Kelley and C. Yanofsky, Proc. Natl. Acad, Sci. USA, 79, 3120-3124 (1982)), the temperature-sensitive λ repressor (cI 857) (J. J. Sninsky et al., Gene, 16, 275-286 (1982)), the repressor of the phosphatase operon (H. Shinagawa et al., J. Mol. Biol., 168,477-488 (1983)), and so on. As means for artificially regulating the binding of these repressor proteins to the operator site, addition of chemicals, regulation of physical conditions such as temperature, and others may be used. For example, the binding of the lac repressor to the lac operator can be inhibited by addition of isopropyl-β-thiogalactopyranoside (IPTG); the binding of the trp repressor to the trp operator can be inhibited by addition of indole acrylic acid (IAA); the binding of the temperature-sensitive λ repressor to the λ operator can be inhibited by increasing culture temperature to 37° C. or higher; and the binding of the repressor of the phosphatase operon to the operator can be inhibited by lowering phosphate ion concentration in the medium.

By inhibiting the binding between the repressor and the operator by the foregoing methods, the promoter inactivated by the repressor can be activated so that the gene which is initially not expressed can be changed to a state such that it is expressed.

The base sequence (b) functioning as the operator and the gene coding for the repressor protein can be incorporated into the same plasmid; alternatively, they can be independently incorporated into two different plasmids capable of co-existing in the same host and the two plasmids can co-exist in the same host cell. In any event, it is sufficient that the repressor protein be capable of binding the operator in host cells.

Further, a gene the expression of which confers resistance to an antibiotic, or the like acting as a selection marker is generally inserted in the plasmid(s).

To introduce the obtained plasmid(s) into Coryneform bacterial cells, conventional methods such as the protoplast method, among others, are applicable.

The invention now being generally described, the same will be better understood by reference to certain specific examples which are included herein for purposes of illustration only and are not intended to be limiting of the invention or any embodiment thereof, unless specified.

EXAMPLES

Example 1

Formation of pEB 001

Figure 1:
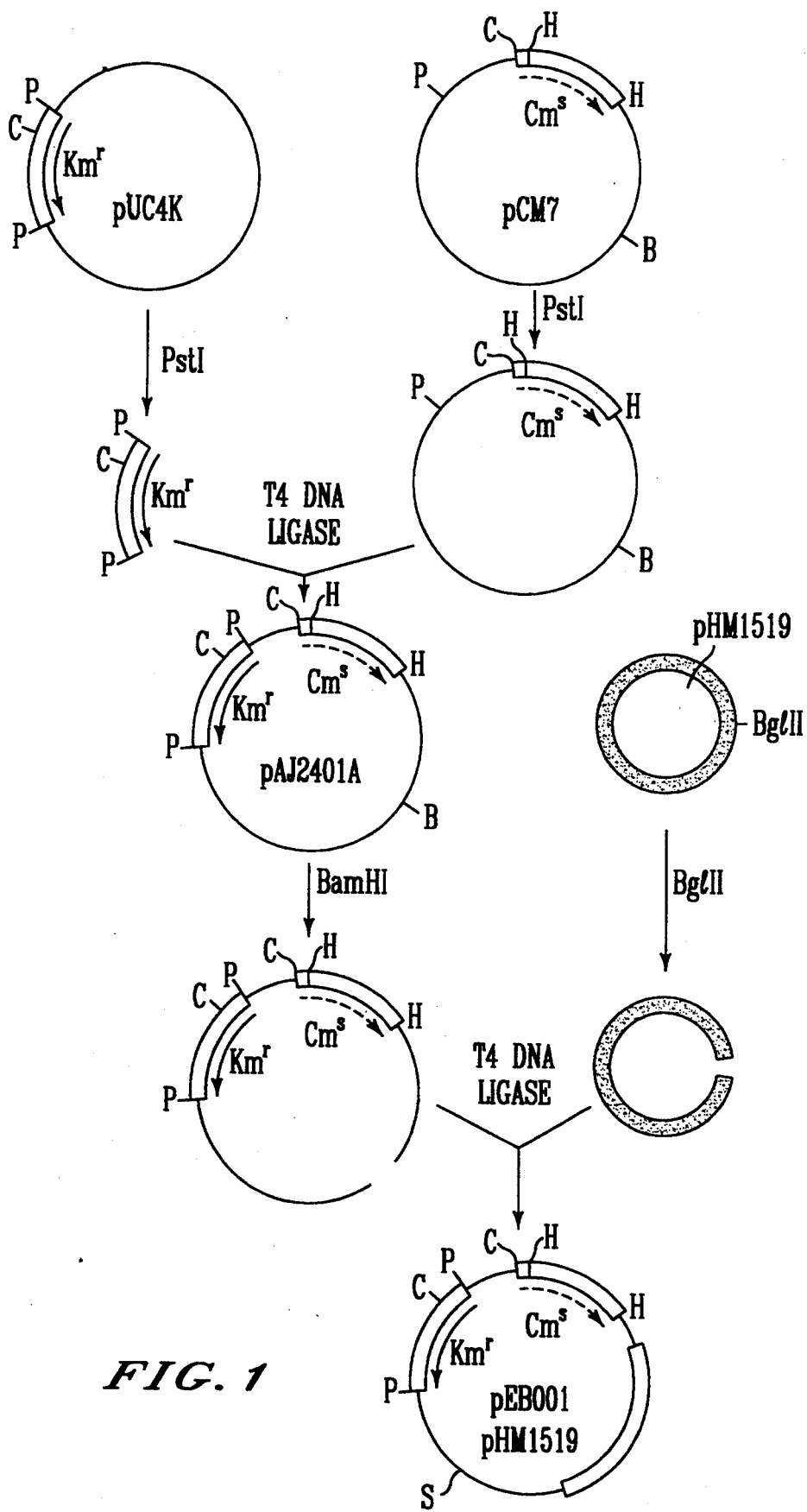
FIG. 1 is a drawing explaining the procedure for constructing a promoter-detecting vector pEB 001. The abbreviations have the following meanings.

Promoter-probing vector pEB 001 carrying a chloramphenicol-resistant gene which had lost a promoter sequence, being capable of replicating in cells of Coryneform bacteria, expressing kanamycin resistance, and carrying a site cleavable by Cla I and Hind III as a site capable of having inserted therein a promoter was formed by the method shown in FIG. 1. That is, plasmid pUC 4K (cf. Gene, 19, 259–268 (1982), and J. Mol. Biol., 147,217–226 (1981)) carrying a kanamycin-resistant gene derived from transposon Tn 903 was first cleaved with Pst I to excise a DNA fragment of about 1.4 kb containing a kanamycin-resistant gene. After mixing with DNA of plasmid pCM 7 (cf. Gene, 20, 305–316 (1982)), containing a structural gene region of a chloramphenicol-resistant gene cleaved with Pst I, ligation was performed using $T_4$ DNA ligase. The obtained recombinant DNA was introduced into *Escherichia coli* HB101 strain to select a strain having kanamycin resistance. From the separated strain, plasmid DNA was obtained. It was confirmed that the kanamycin-resistant gene had been correctly inserted by the size of the plasmid and the fact that a DNA fragment of about 1.4 Kb could be obtained by cleavage with Pst I. This plasmid was named pAJ 2401A. Next, in order to impart a replication ability in cells of Coryneform bacteria to pAJ 2401A, DNA of plasmid pHM 1519 (cf. Published Unexamined Japanese Patent Application 77895/83) capable of replicating in cells of Coryneform bacteria was cleaved with Bgl II followed by mixing with DNA of pAJ 2401A cleaved with BamH I and ligating using $T_4$ DNA ligase. The obtained recombinant DNA was introduced into *Escherichia coli* HB101 strain to select a strain having a kanamycin resistance. From the separated strain, plasmid DNA was obtained. It was confirmed that it was the desired plasmid by the size of the plasmid and by lack of cleavage by BamH I and Bgl II. This plasmid was named pEB 001. pEB 001 was introduced into *Brevibacterium lactofermentum* AJ 12036 (FERM BP-734) and *Corynebacterium glutamicum* ATCC 13060 and a strain having a kanamycin resistance was selected. From the separated strain, plasmid DNA was obtained. It was confirmed that it was DNA of pEB 001 by the size of the plasmid and cleavage patterns with restriction enzymes such as Pst I, BamH I, etc. From these strains, the strain *Brevibacterium lactofermentum*, in which a clear band of DNA of pEB 001 had been detected, was deposited as AJ 12177 (FERM-p7942). As above, pEB 001, which is a shuttle vector capable of replicating in *Escherichia coli*, *Brevibacterium lactofermentum* and *Corynebacterium glutamicum* and expresing kanamycin resistance, carries a structural gene region of the chloramphenicol-resistant gene which has lost the promoter part, and carries a Cla I and Hind III cleavage site as a site capable of inserting a promoter.

DNA of pCM 7 used in this example was prepared from *Escherichia coli* ATCC 37173. DNA of pUC 4K was purchased from Pharmacia Japan Co., Ltd. Further, DNA of pHM 1519 was prepared from *Corynebacterium glutamicum* ATCC 13058, a strain possessing this DNA.

Formation of pEB 003

Promoter-detecting vector pEB 003 carrying a structural gene region of a chloramphenicol-resistant gene which had lost a promoter sequence, being capable of replicating in cells of Coryneform bacteria, expressing kanamycin resistance, and carrying a site cleavable with 5 restriction enzymes (Pst I, HPa I, BamH I, Cla I and Hind III) as a site capable of having a promoter inserted therein was formed by the method shown in FIG. 2. First, DNA from pAJ 2401A was partly cleaved with Pst I. The DNA fragments formed by cleavage at one site were collected by agarose gel and a single strand portion projecting at both edges of the DNA fragments was removed to produce blunt ends. Then, ligation was performed using $T_4$ DNA ligase. The obtained recombinant DNA was introduced into *Escherichia coli* HB101 strain and a strain having a kanamycin resistance was selected. From the separated strain, plasmid DNA was obtained, and plasmid DNA cleaved with Pst I at one site was selected. In these plasmids, a plasmid which had lost the Pst I cleavage site at the 5'-side and a plasmid which had the Pst I cleavage site at the 3'-side of the kanamycin-resistant gene were present. The former plasmid was named pEB 002A and the latter was named pEB 002B. Next, DNA of pEB 001 was cleaved with Cla I and Sal I to obtain DNA fragment A containing the structural gene region of the chloramphenicol-resistant gene and a replication initiation site in cells of Coryneform bacteria. On the other hand, pEB 002A was cleaved with Pst I and Sal I to obtain DNA fragment B containing a kanamycin-resistance gene. Further, an oligonucleotide as shown in FIG. 3 was synthesized according to the phosphite method to prepare DNA fragment C carrying a Pst I cleavage site at the 5'-terminal, a Cla I cleavage site at the 3'-terminal and a Hpa I and BamH I cleavage site therebetween. After mixing DNA fragments A, B and C, they were ligated using $T_4$ DNA ligase. The obtained recombinant DNA was introduced into *Brevibacterium lactofermentum* AJ 12036 (FERM BP-734) and strains having a kanamycin resistance were selected. From the separated strains, plasmid DNA was obtained. It was confirmed that it was the desired plasmid DNA by the size of the plasmid and the cleavage patterns with restriction enzymes such as Pst I, Hpa I, BamH I, etc. This plasmid was named pEB 003. pEB 003 possesses cleavage sites with 5 restriction enzymes (Pst I, Hpa I, BamH I, Cla I and Hind III) as sites where a promoter may be inserted. Among them, the cleavage site with Pst I, Hpa I and BamH I is the only one in the vector which is extremely useful for insertion of a promoter.

*Brevibacterium lactofermentum* AJ 12036 (FERM BP-734) to which pEB 003 had been introduced was deposited as AJ 12178 (FERMP 7943).

Incorporation of a tac promoter and a lac operator into pEB 003

DNA of plasmid pDR 540 (cf. Gene, 20,231 (1982)) (commercially available, purchased from Pharmacia Japan Co., Ltd.) carrying the *Escherichia coli* tac promoter and lac operator was cleaved with BamH I and Pst I. The obtained DNA fragments of about 1100 base pairs containing the tac promoter and the lac operator were fractionated and purified by agarose gel electrophoresis. After mixing with DNA of pEB 003 cleaved with Pst I and BamH I, ligation was performed using $T_4$ DNA ligase. The obtained recombinant DNA was introduced into *Escherichia coli* HB 101 strain and strains having a chloramphenicol resistance were selected. From the separated strains, plasmid DNA was obtained. It was confirmed that it was a plasmid having incorporated therein the *Escherichia coli* tac promoter as desired, by the size of the plasmid and cleavage patterns with restriction enzymes such as Pst I, BamH I, etc. This plasmid was named pEB 003TA.

Next, pEB 003TA was introduced into *Brevibacterium lactofermentum* AJ 12036 (FERM BP-734) and strains having a kanamycin resistance were selected. From the separated strains, a plasmid was obtained. It was confirmed that the plasmid was pEB 003TA by the size of the plasmid and cleavage patterns with restriction enzymes such as Pst I, BamH I, etc.

Formation of a gene expression-regulating vector pEC 701

Plasmid pEC 701, capable of regulating expression of a gene ligated downstream from a tac promoter and a lac operator region by the action of a regulating gene (lac repressor) was formed by the method as shown in FIG. 4.

First, after pEB 003TA (formed as above) was cleaved with Pst I and Sal I, DNA fragment D of about 5.6 kb was recovered from agarose gel. On the other hand, the plasmid pIN III (y. Masui et al., Experimental Manipulation of Gene Expression, Ed. M. Inouye, pp. 15, Academic Press, Inc. 1983) of *Escherichia coli* was cleaved with Pst I, and Sal I, and DNA fragment E of about 5.6 kb containing the lac repressor (lac I) was recovered from agarose gel. Further, plasmid pUC 4K (Gene, 19, 256-268 (1982)) of *Escherichia coli* was cleaved with Pst I, and DNA fragment F of about 1.2 kb containing a kanamycin-resistant gene was likewise recovered from agarose gel. The thus obtained 3 DNA fragments D, E and F were mixed in an approximately equal amount. After ligating with $T_4$ DNA ligase, they were introduced into *Brevibacterium lactofermentum* AJ 12036 (FERM BP-734) and strains showing a kanamycin resistance were selected. From the separated strains, plasmid DNA of about 12.4 kb composed by ligation of 3 DNA fragments D, E and F was obtained. It was confirmed that it was the desired plasmid by cleavage patterns with restriction enzymes such as Pst I, Sal I, etc. This plasmid was named pEC 701. pEC 701 was again introduced into *Brevibacterium lactofermentum* AJ 12036 (FERM BP-734) and *Corynebacterium glutamicum* ATCC 13060, from which strains those showing a kanamycin resistance were selected. From the separated strains, plasmid DNA was obtained. It was confirmed that all DNA was that of pEC 701 by the size of the plasmid and cleavage patterns with restriction enzymes such as Pst I, Sal I, etc.

The thus formed pEC 701 is a shuttle vector carrying a tac promoter, a lac operator and a lactose operon repressor (lac repressor), being capable of replicating in *Escherichia coli*, *Brevibacterium lactofermentum* and *Corynebacterium glutamicum* and expressing a kanamycin resistance. It is also a vector bearing a structural gene region of a chloramphenicol-resistant gene, and is capable of regulating expression of the chloramphenicol-resistant gene by the lac repressor. Further, there are sites which can be cleaved with restriction enzymes such as BamH I, etc. downstream from the lac operator. pEC 701 is also a vector capable of regulating expression of the gene by incorporating a structural gene region free from a promoter of any useful gene, utilizing these sites as cloning sites.

Example 2

Incorporation of a lac promoter and operator into pEB 003

DNA of plasmid pGL 101 (cf. J. Mol. Appl. Genet., 1, 139 (1981)) carrying the *Escherichia coli* lac UV5 promoter and operator was cleaved with Pst I and Pvu II. The obtained DNA fragments of about 1000 base pairs containing the lac UV5 promoter and operator were fractionated and purified by agarose gel electrophoresis. After mixing with the fragments containing the lac UV promoter and operator and DNA of pEB 003 cleaved with Pst I and Hpa I, ligation was performed using $T_4$ DNA ligase. The obtained recombinant DNA was introduced into *Escherichia coli* HB 101 strain and strains having a chloramphenicol resistance were selected. From the separated strains, plasmid DNA was obtained. It was confirmed that it was a plasmid having incorporated therein the *Escherichia coli* lac UV5 promoter and operator as desired, by the size of the plasmid and cleavage patterns with restriction enyzmes such as Pst I, BamH I, etc. This plasmid was named pEB 003LA.

Next, pEB 003LA was introduced into *Brevibacterium lactofermentum* AJ 12036 (FERM BP-734) and strains having a kanamycin resistance were selected. From the separated strains, a plasmid was obtained. It was confirmed that the plasmid was pEB 003LA by the size of the plasmid and cleavage patterns with restriction enzymes such as Pst I, BamH I, etc.

Formation of a gene expression-regulating vector pEC 702

Plasmid pEC 702, capable of regulating expression of a gene ligated downstream from a lac promoter and lac operator region by the action of the lac repressor, was formed by the method shown in FIG. 5. After pEB 003LA was cleaved with Pst I and Sal I, DNA fragment D' of about 5.5 kb containing the lac promoter and operator was recovered from agarose gel. After ligating the fragment D', the Pst I-Sal I fragment E of about 5.6 kb containing the lac repressor (lac I) excised from plasmid pIN II and the Pst I fragment F of about 1.2 kb containing a kanamycin-resistant gene excised from pUC 4K using $T_4$ DNA ligase in a manner similar to Example 1, they were introduced into *Brevibacterium lactofermentum* AJ 12036 (FERM BP-734) and strains showing a kanamycin resistance were selected. From the separated strains, plasmid DNA of about 12.3 kb, composed of 3 ligated DNA fragments D', E and F, was obtained. It was confirmed that it was the desired plasmid by cleavage patterns with restriction enzymes such as Pst I I, Sal I, etc. This plasmid was named pEC 702. pEC 702 was again introduced into *Brevibacterium lactofermentum* AJ 12036 (FERM BP-734) and *Corynebacterium glutamicum* ATCC 13060, from which strains those showing a kanamycin resistance were selected. From the separated strains, plasmid DNA was obtained. It was confirmed that all of this DNA was that of pEC 702 by the size of the plasmid and cleavage patterns with restriction enzymes such as Pst I, Sal I, etc.

The thus formed pEC 702 is a shuttle vector carrying a lac promoter, a lac operator and a lac repressor, being capable of replicating in *Escherichia coli*, *Brevibacterium lactofermentum* and Coryneform, and expressing a kanamycin resistance. It is also a vector bearing a structural gene region of a chloramphenicol-resistant gene and is capable of regulating expression of the chloramphenicol-resistant gene by the lac repressor. Further, there are sites which may be cleaved by restriction enzymes such as BamH I, etc. downstream from the lac operator. pEC 701 is also a vector capable of regulating expression of the gene by incorporating a structural gene region of any useful gene free from a promoter utilizing these sites as cloning sites.

Example 3

Regulation of gene expression using the gene expression-regulating vectors pEC 701 and pEC 702

*Brevibacterium lactofermentum* AJ 12036 (FERM-BP 734) harboring pEC 701 or pEC 702, was inoculated on 50 ml of liquid medium of pH 7.2 containing 1% yeast extract, 1% polypeptone, 0.5% NaCl, 0.5% glucose and 10 μg/ml of kanamycin, followed by shake culture at 30° C. After culturing for 3 hours, 0.2 mM of isopropyl-β-thiogalactopyranoside (IPTG) was supplemented thereto and culture was continued. With passage of time, 5 ml samples of the culture solution were taken and bacteria were collected by centrifugation. After washing, the cells were ground by way of ultrasonic waves and centrifuged at 15,000 r.p.m. for 15 minutes. The supernatant was used as a crude enzyme solution and measured with respect to chloramphenicol acetyltransferase activity. The chloramphenicol acetyltransferase activity was measured by the method of W. V. Shaw, Methods in Enzymology, 43, 737 (1975). Similar runs were also performed on *Brevibacterium lactofermentum* AJ 12036 having no plasmid, AJ 12036 strain harboring plasmid pEB 003TA having a tac promoter and a lac operator but having no lac repressor, and AJ 12036 strain harboring plasmid pEB 003LA having a lac promoter and a lac operator but having no lac repressor. The results are shown in Table 1. It was verified that by the addition of IPTG, the chloramphenicol acetyltransferase activity was enhanced by about 10 fold with the pEC 701-harboring strain and the pEC 702-harboring strain, respectively, as compared to the case where none is added, and gene expression of chloramphenicol acetyltransferase could be artificially regulated by the addition of IPTG in both the pEC 701-harboring strain and the pEC 702harboring strain. On the other hand, in both the pEB 003TA-harboring strain and the pEB 003LA-harboring strain, high activity was noted irrespective of the presence or absence of IPTG and regulation of gene expression was impossible.

TABLE 1

Regulation of chloramphenicol acetyltransferase gene in *Brevibacteriun lactofermentum* AJ 12036 using the gene-expression regulating plasmids pEC 701 and pEC 702

| Plasmid | IPTG | Activity of Chloramphenicol Acetyltransferase | | |
|---|---|---|---|---|
| | | 0 hr | 1 hr | 2 hr |
| None | − | 0 | 0 | 0 |
| | + | 0 | 0 | 0 |
| pEB 003TA | − | 470 | 460 | 320 |
| | + | 470 | 460 | 300 |
| pEC 701 | − | 18 | 23 | 28 |
| | + | 18 | 101 | 205 |
| pEB 003LA | − | 168 | 166 | 160 |
| | + | 168 | 165 | 155 |
| pEC 702 | − | 6 | 6 | 5 |
| | + | 6 | 42 | 36 |

Example 4

Incorporation of a trp promoter and a trp operator into pEB 003

DNA of plasmid pDR 720 (cf. Gene, 20 231 (1982)) (commercially available, purchased from Pharmacia Japan Co., Ltd.) carrying the *Escherichia coli* trp promoter and trp operator was cleaved with Pst I. The obtained DNA fragments of about 1100 base pairs containing the trp promoter and trp operator were fractionated and purified by agarose gel electrophoresis. After mixing the DNA fragments with DNA of pEB 003 cleaved with Pst I, ligation was performed using T4 DNA ligase. The obtained recombinant DNA was introduced into *Escherichia coli* HB 101 strain and strains having a chloramphenicol resistance were selected. From the separated strains, plasmid DNA was obtained. It was confirmed that it was a plasmid having incorporated therein the *Escherichia coli* trp promoter and trp operator as desired, by the size of the plasmid and cleavage patterns with restriction enzymes such as Pst I, Pvu I, etc. This plasmid was named pEB 003TR.

Next, pEB 003TR was introduced into *Brevibacterium lactofermentum* AJ 12036 (FERM BP-734) and strains having a kanamycin resistance were selected. From the separated strains, a plasmid was obtained. It was confirmed that the plasmid was pEB 003TR by the size of the plasmid and cleavage patterns with restriction enzymes such as Pst I, Pvu I, etc.

Formation of a gene expression-regulating vector pEC 801

Plasmid pEC 801 capable of regulating expression of a gene ligated downstream from a trp promoter and trp operator region by the action of a regulating gene (trp repressor) was formed by the method shown in FIG. 6. First, pEB 003TR (formed as above) was cleaved with Sal I. On the other hand, *Escherichia coli* plasmid ptrp R3 (W. Roeder and R. L. Somerville, Mol. Gene. Genet., 176,361 (1979)) was cleaved with BamH I and, about 1200 base pairs of DNA fragments containing the trp repressor (trpR) were recovered from agarose gel. The thus obtained two DNA's were ligated with T4 DNA ligase via a synthesized DNA adaptor synthesized by the phosphite method. Thereafter, they were introduced into *Brevibacterium lactofermentum* AJ 12036 (FERM BP-734) and strains showing a kanamycin resistance were selected. From the separated strains, plasmid DNA of about 9.7 kb composed by ligation of the above-described 2 DNA fragments was obtained. It was confirmed that it was the desired plasmid by the cleavage pattern with BamH I. This plasmid was named pEC 801. pEC 801 was again introduced into *Brevibacterium lactofermentum* AJ 12036 (FERM BP-734) and *Corynebacterium glutamicum* ATCC 13060, from which strains those showing a kanamycin resistance were selected. From the separated strains, plasmid DNA's were obtained. It was confirmed that all of these were DNA of pEC 801 by the size of the plasmid and the cleavage pattern with BamH I.

The thus formed pEC 801 is a shuttle vector carrying a trp promoter, a trp operator and a trp repressor, which is capable of replicating in *Escherichia coli*, *Brevibacterium lactofermentum* and *Corynebacterium glutamicum* and expressing a kanamycin resistance. It is also a vector bearing a structural gene region of a chloramphenicol-resistant gene and is capable of regulating expression of the chloramphenicol-resistant gene by the trp repressor. Further, there are sites which may be cleaved with restriction enzymes such as Pst I, Hpa I, BamH I, etc. downstream from the trp promoter. pEC 701 is also a vector capable of regulating expression of the gene by incorporating a structural gene region free from a promoter, of any useful gene, utilizing these sites as cloning sites.

Regulation of gene expression using the gene express-regulating vector pEC 801

*Brevibacterium lactofermentum* AJ 12036 (FERM-BP 734) harboring pEC 801 was inoculated on 50 ml of liquid medium of pH 7.2 containing 1% yeast extract, 1% polypeptone, 0.5% NaCl, 0.5% glucose and 10 μg/ml of kanamycin followed by shake culture at 30° C. After culturing for 3 hours, 0.13 mM of indole acrylic acid (IAA) was supplemented and culture was continued. With passage of time, 5 ml samples of the culture solution were taken and bacteria were collected by centrifugation. After washing, the cells were ground by way of ultrasonic waves and centrifuged at 15,000 r.p.m. for 15 minutes The supernatant was used as a crude enzyme solution and measured with respect to chloramphenicol acetyltransferase activity. The chloramphenicol acetyltransferase activity was measured by the method of W. V. Shaw, Methods in Enzymology, 43, 737 (1975). Similar runs were also performed on *Brevibacterium lactofermentum* AJ 12036 having no plasmid, the AJ 12036 strain harboring plasmid pEB 003TR having a trp promoter and a trp operator but having no trp repressor. The results are shown in Table 2. It was verified that by the addition of IAA, the chloramphenicol acetyltransferase activity was enhanced by about 5 fold with the pEC 801-harboring strain, as compared to the case where none is added, and gene expression of chloramphenicol acetyltransferase could be artificially regulated by the addition of IAA in the pEC 801-harboring strain. On the other hand, in the case of a pEB 003TR-harboring strain having no trp repressor, high activity was noted irrespective of the presence or absence of IAA and regulation of gene expression was impossible.

TABLE 2

Regulation of chloramphenicol acetyltransferase gene in *Brevibacterim lactofermentum* AJ 12036 using the gene-expression regulating plasmid pEC 801

| Plasmid | IAA | Activity of Chloramphenicol Acetyltransferase | | |
|---|---|---|---|---|
| | | 0 hr | 1 hr | 2 hr |
| None | − | 0 | 0 | 0 |
| | + | 0 | 0 | 0 |
| pEB 003TR | − | 252 | 256 | 251 |
| | + | 252 | 255 | 250 |
| pEC 801 | − | 15 | 21 | 23 |
| | + | 15 | 100 | 102 |

(unit: nmol/min. mg)

Example 5

Formation of a gene expression-regulating vector pEC 901

Plasmid pEC 901 capable of regulating expression of a gene ligated downstream from a $P_RP_L$ promoter and operator region of lambda phage by the action of a temperature-sensitive cI 857 repressor was formed by the method as shown in FIG. 7. After pMY 12-6 (Mol. Gen. Genet., 187, 79–86 (1982)) was cleaved with Pst I and BamH I, DNA fragments of about 1.35 kb containing a $P_RP_L$ promoter operator and cI 857 repressor were recovered from agarose gel. On the other hand, pEP 003 was cleaved with Pst I and BamH I, and DNA fragments of about 7.4 kb were recovered from agarose gel. The two DNA fragments were ligated with T4 DNA ligase and then introduced into *Escherichia coli* HB 101, and strains showing a kanamycin resistance were selected. From the separated strains, plasmid DNA of about 8.7 kb formed by ligation of the 2 DNA fragments was obtained. It was confirmed that it was the desired plasmid by cleavage patterns with restriction enzymes such as Pst I, BamH I, etc. This plasmid was named pEC 901. pEC 901 was introduced into *Brevibacterium lactofermentum* AJ 12036 (FERM BP-734) and *Corynebacterium glutamicum* ATCC 13060, from which strains those showing a kanamycin resistance were selected. From the separated strains, plasmid DNA was obtained. It was confirmed that all of the DNA was that of pEC 901 by the size of the plasmid and cleavage pattern with restriction enzymes such as Pst I, BamH I, etc.

The thus formed pEC 901 is a shuttle vector carrying a lambda phage $P_RP_L$ promoter, operator and cI 857 repressor, being capable of replicating in *Escherichia coli*, *Brevibacterium lactofermentum* and *Corynebacterium glutamicum* and expressing a kanamycin resistance. It is also a vector bearing a structural gene region of a chloramphenicol-resistant gene and capable of regulating expression of the chloramphenicol-resistant gene by temperature using the cI 857 repressor. Further, there are sites which may be cleaved with restriction enzymes such as BamH I, Cla I, etc. downstream from the $P_RP_L$ promoter. pEC 901 is also a vector capable of regulating expression of the gene by incorporating a structural gene region of any useful gene free from a promoter, utilizing these sites as cloning sites.

Regulation of gene expression using the gene expression-regulating vector pEC 901

*Brevibacterium lactofermentum* AJ 12036 (FERM-BP 734) harboring pEC 901 was inoculated on 50 ml of liquid medium of pH 7.2 containing 1% yeast extract, 1% polypeptone, 0.5% NaCl, 0.5% glucose and 10 μg/ml of kanamycin followed by shake culture at 30° C. When the OD570 reached 0.4, the culture solution was treated at 43° C. for 5 minutes followed by shake culture at 39° C. With passage of time, 20 ml samples of the culture solution were taken and bacterial cells were collected by centrifugation. After washing, the cells were ground via ultrasonic waves and centrifuged at 15,000 r.p.m. for 15 minutes. The supernatant was used as a crude enzyme solution and measured with respect to chloramphenicol acetyltransferase activity. The chloramphenicol acetyltransferase activity was measured by a method similar to Example 3. Similar runs were also performed on *Brevibacterium lactofermentum* AJ 12036 having pEB 003. The results are shown in Table 3. By elevating the temperature, the chloramphenicol acetyltransferase activity was expressed in the pEC 901-harboring strain and in the case where no temperature was elevated, the activity was not observed. On the other hand, no enhancement of the chloramphenicol acetyltransferase activity due to elevation of the temperature was noted in the case of the pEB 003-harboring strain.

TABLE 3

Regulation of chloramphenicol acetyltransferase gene in
Brevibacterium lactofermentun AJ 12036 using the gene-
expression regulating plasmid pEC 901

| Plasmid | Culture Temperature | Activity of Chloramphenicol Acetyltransferase | | |
|---------|---------------------|---|---|---|
| | | 0 hr | 6 hr | 24 hr |
| pEB 003 | 30° C. | 29 | 33 | 18 |
| | 40° C. | 29 | 17 | 17 |
| pEC 901 | 30° C. | 0 | 0 | 0 |
| | 40° C. | 0 | 80 | 103 |

(unit: nmol/min. mg)

Example 6

Regulation of gene expression in the presence of more than one plasmid

With respect to a method for regulating gene expression by incorporating an operator and a gene coding for a repressor protein in separate plasmids and having them co-exist in the same host cell, an example using a trp operator and a trp repressor is shown below. However, the combination of operator and repressor is not limited to the combination of a trp operator and a trp repressor shown in this example but may be any combination of a lac operator and a lac repressor, lambda phage, $P_R P_L$ operator and lambda phage repressor (cI 857 repressor, etc.), or the like.

As a plasmid bearing a trp promoter, trp operator and chloramphenicol acetyltransferase gene, pEB 003TR formed in Example 4 was used. In the case where pEB 003TR alone was introduced into Brevibacterium lactofermentum AJ 12036 (FERM BP-734), it was impossible to regulate the chloramphenicol acetyltransferase activity, as shown in Example 4.

As the plasmid bearing a trp repressor gene, any repressor can be used as long as it can co-exist with pEB 003TR in Coryneform bacterial cells and produces a repressor. For example, pEC 830 obtained by incorporating a trp repressor gene into trimethoprim-resistant plasmid vector pAJ 228, and the like, can be used.

Formation of plasmid vector pAJ 228

(1) Trimethoprim-resistant variant AJ 12146 (FERM-P 7672) derived from mutation of Brevibacterium lactofermentum AJ 12036 was inoculated on a 1 liter CM2G medium (1 g/dl of peptone, 1 g/dl of yeast extract, 0.5 g/dl of glucose and 0.5 g/dl of NaCl, adjusted pH to 7.2) followed by shake culture at 30° C. for about 3 hours. Bacterial cells were collected at the exponential growth phase. After the cells were lysed with lysozyme-SDS, chromosomal DNA was extracted and purified by conventional treatment with phenol to finally obtain 3.0 mg of DNA.

Brevibacterium lactofermentum AJ 12146 was obtained by contacting Brevibacterium lactofermentum AJ 12036 with 1,000 μg/ml of N-methyl-N'-nitro-N-nitrosoguanidine at 0° C. for 20 minutes for variation treatment and separating a strain capable of growing in minimum medium (containing 2 g/dl of glucose, 1 g/dl of ammonium sulfate, 0.25 g/dl of urea, 0.1 g/dl of $KH_2PO_4$, 0.04 g/dl of $MgSO_4 \cdot 7H_2O$, 200 μg/l of thiamine hydrochloride, 50 μg/l of biotin, 2 ppm of iron irons, 2 ppm of manganese ions and 1.5 g/dl of agar, pH adjusted to 7.0) supplemented with 100 μg/ml of trimethoprim.

(2) As the vector, pAM 330 was used. pAM 330 was prepared as follows:

First, Brevibacterium lactofermentum ATCC 13869 having pAM 330 as plasmids was inoculated on 100 ml of CM2G medium. After culturing at 30° C. to reach late exponential growth phase, the cells were lysed by lysozyme and SDS. The supernatant was obtained by ultracentrifugation of 30,000 x g for 30 minutes. After treatment with phenol, 2 volumes of ethanol were added to recover DNA as a precipitate. After the DNA was dissolved in a small quantity of TEN buffer (20 mM tris-hydrochloride, 20 mM NaCl, 1 mM EDTA, pH 8.0), the solution was subjected to agarose gel electrophoresis for separation. Then, the separated product was taken out to obtain about 15 μg of DAM 330 DNA.

(3) The chromosomal DNA, 20 μg, obtained in (1) and 10 μg of the plasmid DNA obtained in (2) were treated with restriction endonuclease Mbo I at 37° C. for 30 minutes, respectively, to effect partial cleavage. After heat treatment at 65° C. for 10 minutes, both reaction solutions were mixed with each other, and the mixture was subjected to a ligation reaction of DNA strands with $T_4$ phage-derived DNA ligase at 10° C. for 24 hours in the presence of ATP and dithiothreitol. After heat treatment at 65° C. for 10 minutes, a 2-fold volume of ethanol was added to the reaction solution to precipitate and harvest DNA after completion of the ligation reaction.

(4) Brevibacterium lactofermentum AJ 12036 sensitive to trimethoprim was used as recipient. As the transformation method, a protoplast transformation method was used. First, the cells were cultured in 5 ml of CM2G medium to reach an early exponential growth phase. After adding 0.6 units/ml of penicillin, shake culture was conducted for an additional 1.5 hours. Cells were harvested by centrifugation and washed with 0.5 ml of SMMP medium (pH 6.5) composed of 0.5 M sucrose, 20 mM maleic acid, 20 mM magnesium chloride and 3.5% Pennassay broth (Difco) and then suspended in SMMP medium containing 10 mg/ml of lysozyme. The suspension was treated at 30° C. for 20 hours to obtain protoplasts. After centrifuging at 6000 x g for 10 minutes, the protoplasts were washed with SMMP and resuspended in 0.5 ml of SMMP. The thus obtained protoplasts were mixed with 10 μg of DNA prepared in (3) in the presence of 5 mM EDTA. After polyethylene glycol was added to the mixture to reach the final concentration of 30%, the mixture was allowed to stand at room temperature for 2 minutes to incorporate DNA into the protoplasts. After the protoplasts were washed with 1 ml of SMMP medium, they were resuspended in 1 ml of SMMP, and the suspension was cultured at 30° C. for 2 hours for phenotypic expression. The culture solution was spread over a protoplast renaturation medium of pH 7.0. The renaturation medium contained, per one liter of distilled water, 12 g of tris(hydroxymethyl)aminomethane, 0.5 g of KCl, 10 g of glucose, 8.1 g of $MgCl_2 \cdot 6H_2O$, 2.2 g of $CaCl_2 \cdot 2H_2O$, 4 g of peptone, 4 g of yeast extract powder, 1 g of Casamino Acid (Difco), 0.2 g of $K_2HPO_4$, 135 g of sodium succinate, 8 g of agar and 25 μg/ml of trimethoprim (Sigma Co., Ltd.).

After culturing at 30° C. for 1 week, about 100 colonies appeared, which were transferred to minimum medium plates which contained 2% glucose, 1% ammonium sulfate, 0.25% urea, 0.1% $KH_2PO_2$, 0.04% $MgSO_4 \cdot 7H_2O$, 2 ppm of iron ions, 2 ppm of manganese ions, 200 μg/l thiamine hydrochloride and 50 μg/l biotin, pH 7.0, 1.8% agar and 50 μg/ml trimethoprim) by the replica plating method to obtain a strain resistant to trimethoprimo (5) From the strain, a lysate was prepared by the method described in (2). When plasmid DNA was detected by agarose gel electrophoresis, a plasmid obviously larger than vector pAM 330 was detected. This strain was named AJ 12147 (FERM-P 7673).

(6) To confirm that the trimethoprim-resistant genes were present on plasmids (pAJ 228) possessed by AJ 12147, Brevibacterium lactofermentum AJ 12036 was again transformed using the plasmid DNA.

Among colonies which appeared and which had trimethoprim-resistance, 10 colonies each were chosen and collected and the plasmid DNA was detected by agarose gel electrophoresis. In all of them, plasmids having the same size as that of pAJ 228 were present. It became clear that genes expressing trimethoprim resistance were present on the recombinant plasmids described above.

(7) Properties of pAJ 228 DNA (a) The molecular weight of pAJ 228 was determined by agarose gel electrophoresis. Agarose gel electrophoresis was -performed in accordance with the method of P. A. Sharp, et al. (Biochemistry, 12, 3055 (1973)) using 0.8% gel at a constant voltage of 5 V per cm of gel length for 15 hours. The molecular weight was calculated by comparing mobility with that of a molecular weight marker having a known molecular weight: λ phage Hind III fragment (BRL Co., Ltd.) subjected to reaction with 0.5 units of restriction enzyme Cla I for cleaving 1 portion of pAJ 228 with 0.5 μg of pAJ 228 at 37° C. for 1 hour, which was determined to be 7.6 kb.

(b) Preparation of a restriction map of pAJ 228 DNA

A commercially available restriction enzyme from BRL was used. Cleavage of pAJ 228 DNA with the restriction enzyme was carried out using at least a 3 fold excess of enzyme under given conditions with respect to each enzyme. In the case where plasmid DNA was cleaved with one or more restriction enzymes for the purpose of a restriction map, fragments cleaved with a first restriction enzyme were isolated by agarose gel for separation in accordance with the method of Tanaka et al. (T. Tanaka and B. Weisblum, J. Bacteriol., 121, 354 (1975)), condensed by ethanol precipitation and then cleaved with a second restriction enzyme. The cleaved fragments were subjected to agarose gel electrophoresis and their molecular weights were calculated to prepare a restriction map (FIG. 8).

Formation of a gene expression-regulating vector pEC 830

A trimethoprim-resistant vector pEC 830 for regulating gene expression having incorporated therein a trp repressor, was formed by the method shown in FIG. 9. First, plasmid ptrp R3 was cleaved with BamH I as in Example 4, and about 1200 base pairs of DNA fragments containing a trp repressor (trp R) were recovered from agarose gel. Next, the DNA fragments were reacted with DNA polymerase (Klenow fragment) in the presence of 4 deoxynucleotides (dATP, dGTP, dCTP, dTTP) to convert the edges of the fragments into smooth terminals. The thus prepared DNA fragments and DNA of pAJ 228 cleaved with Hpa I were mixed. After ligating them using T4 DNA ligase, they were introduced into Brevibacterium lactofermentum AJ 12036 (FERM BP-734), and strains having a trimethoprim resistance were selected. Plasmids present in the separated strains were extracted. It was confirmed that it was the desired plasmid of about 8.8 kb by the size. This plasmid was named 'pEC 830. pEC 830 was again introduced into Brevibacterium lactofermentum AJ 12036 (FERM BP-734) and strains having a trimethoprim resistance were selected. From the separated strains, plasmid DNA was obtained. It was confirmed that both were DNA of 'pEC 830 by the size of the plasmid and cleavage ,pattern with Xba I.

Regulation of gene expression using the gene expression-regulating vector pEC 830 pEC 830 DNA was introduced into Brevibacterium lactofermentum AJ 12036 (FERM-BP 734) harboring plasmid pEB 003TR carrying a trp promoter and a trp operator formed in Example 4. The thus obtained strain harboring both pEB 003TR and pEC 830 was inoculated on 50 ml of liquid medium containing 10 μg/ml of kanamycin and 50 μg/ml of trimethoprim and having a composition of 1% yeast extract, 1% polypeptone, 0.5% NaCl and 0.5% glucose followed by shake culture at 30° C. After culturing for 3 hours, 0.13 mM of indole acrylic acid (IAA) was supplemented and culture was continued. With passage of time, 5 ml samples of the culture solution were taken and the chloramphenicol acetyltransferase activity was measured by the method shown in Example 4. Similar runs were also performed on the AJ 12036 strain carrying pEB 003TR or pEC 830 singly and the AJ 12036 strain harboring no plasmid. The results are shown in Table 4. It was verified that by the addition of IAA, the chloramphenicol acetyltransferase activity was enhanced by about 3 to 4 fold with the strain harboring both pEB 003TR and pEC 830, as compared with the case of no addition of IAA. Thus, the gene expression could be artifically regulated by the addition of IAA. On the other hand, in the case of the strain harboring pEB 003TR singly, high activity was noted irrespective of the presence or absence of IAA, and regulation of gene expression was impossible.

TABLE 4

Regulation of chloramphenicol acetyltransferase gene in Brevibacterium lactofermentum AJ 12036 using the gene-expression regulating plasmid pEC 830

| Plasmid | IAA | Activity of Chloramphenicol Acetyltransferase | | |
|---|---|---|---|---|
| | | 0 hr | 1 hr | 2 hr |
| None | − | 0 | 0 | 0 |
| | + | 0 | 0 | 0 |
| pEB 003TR | − | 210 | 225 | 218 |
| | + | 200 | 230 | 230 |
| pEC 830 | − | 0 | 0 | 0 |
| | + | 0 | 0 | 0 |
| pEB 003TR, | − | 25 | 27 | 28 |
| pEC 830 | + | 26 | 95 | 110 |

(unit: nmol/min. mg)

Cultures of cell lines containing the plasmids identified below were deposited with the Fermentation Research Institute, Agency of Industrial Science and Technology, Ministry of International Trade and Industry, 1-3, Higashi 1-Chome, Yatabe-Machi, Tsukuba-Gun, Ibaraki-Ken 305, Japan, under the provisions of the Budapest Treaty, on the dates indicated below. The cultures can be accessed under the identification numbers indicated below:

The invention now being fully described, it will be apparent to one of ordinary skill in the art that many changes and modifications can be made thereto without departing from the spirit or scope of the invention as set forth herein.

What is claimed as new and desired to be secured by letters patent of the United States is:

| PLASMID | DATE OF DEPOSIT | FERM-BP | FERM |
|---|---|---|---|
| pEC 701 | Sept. 30, 1991 | BP-3572 | |
| pEC 801 | Sept. 21, 1991 | BP-3573 | |
| pEC 901 | Sept. 21, 1991 | BP-3575 | |
| pEC 830 | Sept. 21, 1991 | BP-3574 | |
| pEB 003 | Nov. 13, 1986 | BP-1201 | P-7943 |

1. A recombinant plasmid vector which is selected from the group consisting of pEC 701, pEC 801, pEC 830, and pEC 901.

2. A Coryneform bacterium containing therein a plasmid vector, said plasmid vector being selected from the group consisting of pEC 701, pEC 801, pEC 830, and pEC 901.

* * * * *

UNITED STATES PATENT AND TRADEMARK OFFICE
CERTIFICATE OF CORRECTION

PATENT NO.   :  5,426,050
DATED        :  June 20, 1995
INVENTOR(S)  :  Yasushi MORINAGA, et al.

It is certified that error appears in the above-indentified patent and that said Letters Patent is hereby corrected as shown below:

On the title page, Item [75], the first inventor's city of residence should read:

--Yokohama--

Signed and Sealed this

Nineteenth Day of September, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,426,050
DATED : JUNE 20, 1995
INVENTOR(S) : YASUSHI MORINAGA ET AL

It is certified that error appears in the above-indentified patent and that said Letters Patent is hereby corrected as shown below:

Column 4, line 29, "X" should read --$\lambda$--.

Column 7, line 27, "Expermental" should read --Experimental--.

Column 9, line 47, "702harboring" should read --702-harboring-.

Column 11, line 22, "minutes The" should read --minutes. The--.

Column 14, line 15, "DAM" should read --pAM--.

Column 15, line 24, "was -performed" should read --was performed--.

Column 16, lines 3 and 8, "'pEC 830" should read --pEC 830--.

UNITED STATES PATENT AND TRADEMARK OFFICE
CERTIFICATE OF CORRECTION

PATENT NO. : 5,426,050
DATED : JUNE 20, 1995
INVENTOR(S) : YASUSHI MORINAGA ET AL

It is certified that error appears in the above-indentified patent and that said Letters Patent is hereby corrected as shown below:

Column 16, line 54, Table 4, last entry under "0 hr", "26" should read --25--.

Column 16, line 66 should read

| -- PLASMID | DATE OF DEPOSIT | FERM-BP | FERM |
|---|---|---|---|
| pEC 701 | Sept. 30, 1991 | BP-3572 | |
| pEC 801 | Sept. 21, 1991 | BP-3573 | |
| pEC 901 | Sept. 21, 1991 | BP-3575 | |
| pEC 830 | Sept. 21, 1991 | BP-3574 | |
| pEB 003 | Nov. 13, 1986 | BP-1201 | P-7943-- |

UNITED STATES PATENT AND TRADEMARK OFFICE
CERTIFICATE OF CORRECTION

PATENT NO. : 5,426,050
DATED : JUNE 20, 1995
INVENTOR(S) : YASUSHI MORINAGA ET AL

It is certified that error appears in the above-indentified patent and that said Letters Patent is hereby corrected as shown below:

Column 17, lines 9-17 through column 18, lines 1-7, delete the Table in its entirety.

Signed and Sealed this

Fourth Day of March, 1997

Attest:

BRUCE LEHMAN

Attesting Officer

Commissioner of Patents and Trademarks